United States Patent [19]

Müller et al.

[11] Patent Number: 5,328,638

[45] Date of Patent: Jul. 12, 1994

[54] OPTICALLY ACTIVE ESTERS OF 5-ETHYL- AND 5-VINYL-1,3-DIOXOLANE-4-CARBOXYLIC ACID, THEIR USE AS DOPING SUBSTANCES IN LIQUID CRYSTAL MIXTURES AND THE LIQUID CRYSTAL MIXTURES CONTAINING THE NEW ESTERS

[75] Inventors: Ingrid Müller, Hofheim am Taunus; Hans-Rolf Dübal, Königstein/Taunus; Claus Escher, Mühltal; Wolfgang Hemmerling, Sulzbach; Gerhard Illian, Frankfurt am Main; Mikio Murakami, Königstein/Taunus; Dieter Ohlendorf, Liederbach; Rainer Wingen, Hattersheim am Main, all of Fed. Rep. of Germany

[73] Assignee: Hoechst Aktiengesellschaft, Frankfurt am Main, Fed. Rep. of Germany

[21] Appl. No.: 881,520

[22] Filed: May 12, 1992

Related U.S. Application Data

[63] Continuation of Ser. No. 410,949, Sep. 22, 1989, abandoned.

[30] Foreign Application Priority Data

Sep. 24, 1988 [DE] Fed. Rep. of Germany ....... 3832503

[51] Int. Cl.$^5$ ............................................. C09K 19/34
[52] U.S. Cl. ........................... 252/299.61; 252/299.01
[58] Field of Search ...................... 252/299.01, 299.61; 359/101, 105

[56] References Cited

U.S. PATENT DOCUMENTS 4,988,459  1/1991  Scherowsky et al. ......... 252/299.61

FOREIGN PATENT DOCUMENTS 0307880  3/1989  European Pat. Off. .
3604898  8/1987  Fed. Rep. of Germany .
3713273  11/1988  Fed. Rep. of Germany .

OTHER PUBLICATIONS

Advanced Org. Chem., March, 2nd Ed., McGraw-Hill, pp. 363-365.
Synthesis, Sep. 1987 (9), pp. 801-806.
Beau et al., Tetrahedron Letters, vol. 26, No. 50, pp. 6193-6196 (1985).
Chemical Abstracts, vol. 110, No. 20, 110:183 512a (May 15, 1989).

Primary Examiner—Philip Tucker
Attorney, Agent, or Firm—Curtis, Morris & Safford

[57] ABSTRACT

Optically active 1,3-dioxolane derivatives of the general formula (I)

$$R^1-(-A^1)_j(-M^1)_k(-A^2)_l(-M^2)_m-(-A^3)_n-X- \quad (I)$$

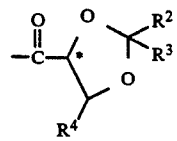

are suitable as doping substances in liquid crystal mixtures. The symbols in the general formula have the following meaning:

$R^1$ has the structure which is analogous to the moiety of the general formula which is on the right of X or is an alkyl or alkylene radical which can be substituted, $R^2$, $R^3$ are H or alkyl, which can also be substituted [$R^2$, $R^3$ can also be a cycloaliphatic compound together with C(2) of the dioxolane ring], $R^4$ is vinyl or ethyl, with the proviso that at least one radical $R^4$ is vinyl or ethyl, if $R^1$ is analogous to the moiety of the formula (I) which is on the right of X, $-A^1$, $-A^2$, $-A^3$ are an aromatic, heterocyclic or aliphatic ring system, $-M^1$, $-M^2$ are $-CO-O$, $-O-CO$, $-CH_2CH_2$, $-CH=CH$, $-CH_2O$, $-OCH_2$, $-C\equiv C$ and X is O, S or O—CO—O.

The particular advantage of the compound of the general formula (I) is that it can induce a high twisting capacity in a cholesteric phase.

3 Claims, No Drawings

OPTICALLY ACTIVE ESTERS OF 5-ETHYL- AND 5-VINYL-1,3-DIOXOLANE-4-CARBOXYLIC ACID, THEIR USE AS DOPING SUBSTANCES IN LIQUID CRYSTAL MIXTURES AND THE LIQUID CRYSTAL MIXTURES CONTAINING THE NEW ESTERS

This application is a continuation of application Ser. No. 07/410,949, filed Sep. 22, 1989, now abandoned.

The German Patent Application P 3,713,273.3 relates to optically active 1,3-dioxolane-4-carboxylic esters. They lead, even in small amounts, to short switching times in tilted smectic phases and to high electroclinic coefficients in orthogonally smectic phases. In particular, the pitch of the helix induced by the doping is so large that compensation by means of other doping substances is not necessary. These are compounds of the general formula

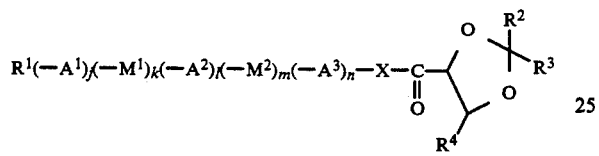

in which the symbols have the following meaning:

$R^1$ is

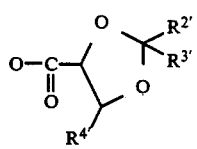

a straight-chain or branched alkyl radical having 1 to 16 carbon atoms or a straight-chain or branched alkenyl radical having 2 to 16 carbon atoms, it being possible for these radicals themselves to contain asymmetric carbon atoms, in which one or more non-adjacent —CH$_2$— groups can be replaced by

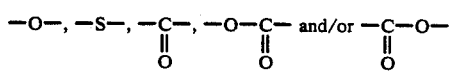

and one or more H can be replaced by F, Cl, Br or CN, $R^2$, $R^{2'}$, $R^3$ and $R^{3'}$ are each H or an alkyl radical having 1 to 10 carbon atoms, in which one or more H can be replaced by F, or $R^2$ and $R^3$ or $R^{2'}$ and $R^{3'}$ together with the C(2) atom of the dioxolane ring form a cyclopentane, cyclohexane or cycloheptane ring, $R^4$, $R^{4'}$ are H or an alkyl radical having 1 to 10 or an alkenyl radical having 2 to 10 carbon atoms, j and l are zero, 1 or 2, k and m are zero or 1, n is zero, 1 or 2, with the following proviso: if j and-/or l are zero, k is zero; if n is zero, m is zero; the sum j+l+n is at least 1 and at most 3, —A$^1$ and —A$^2$ are

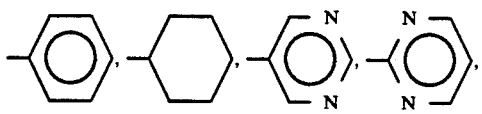

-continued

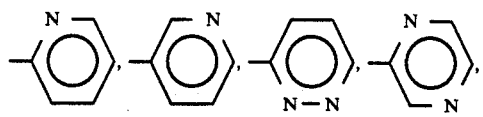

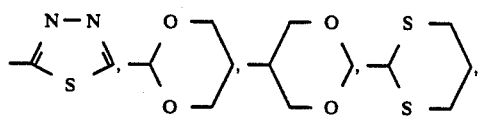

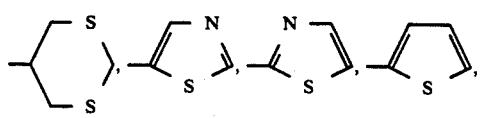

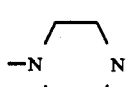

—A$^3$ is

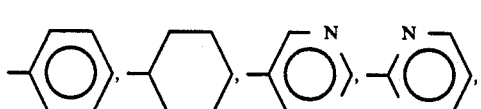

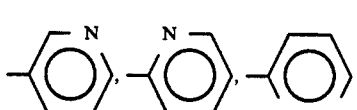

—M$^1$ and M$^2$ are

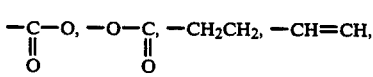

—CH$_2$O, —OCH$_2$ and X is O or S.

In a preferred embodiment, the symbols in the general formula (I) have the following meaning:

$R^1$ is a straight-chain or branched alkyl or alkenyl radical having 4 to 14 carbon atoms, which can contain an asymmetric carbon atom, or in which a —CH$_2$— group can be replaced by

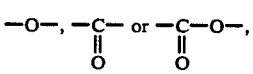

or in which one or more H can be replaced by F, $R^2$, $R^3$, $R_4$, H or an alkyl radical having 1 to 5 carbon atoms or $R^2$, $R^3$ together with the C(2) atom of the dioxolane ring form a cyclopentane or cyclohexane ring, j and l are zero or 1, k, m, n are zero or 1, —M$^1$, —M$^2$ are

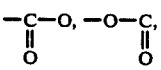

X is O or S.

In a further preferred embodiment, 1,3-dioxolane-4-carboxylic esters of the general formula (IV) are used

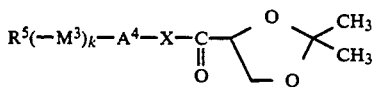 (IV)

in which the symbols have the following meanings:

R⁵ is a straight-chain or branched alkyl or alkenyl radical having 6 to 12 carbon atoms, which can contain an asymmetric carbon atom, —M³ is —O, —S, —O—$\overset{\text{O}}{\underset{\|}{\text{C}}}$— or —$\overset{\text{O}}{\underset{\|}{\text{C}}}$—

—A⁴ is 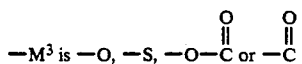,

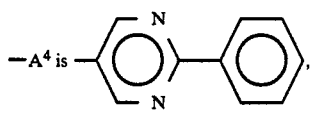,

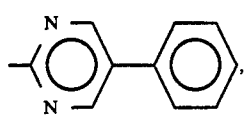,

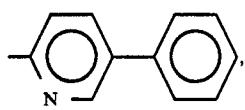,

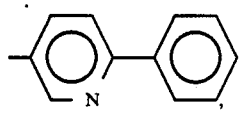,

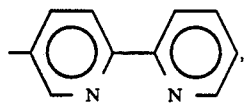,

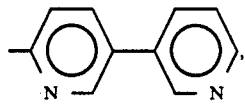,

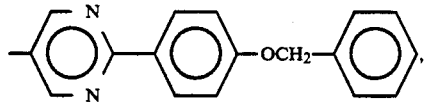,

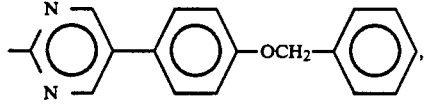,

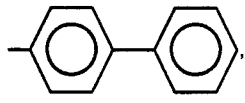,

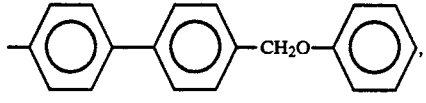,

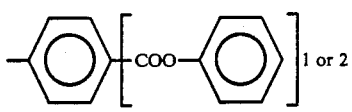

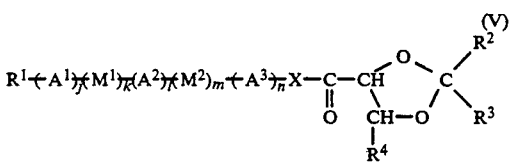

The values for spontaneous polarization (Ps) of the compounds described in the German patent application are in the range of about 8–14 nC/cm² at 25° C. and 10 mol % of doping of the tilted smectic liquid crystal phase and in the range of about 80–140 nC/cm² upon linear extrapolation to the pure compound.

Surprisingly, it has now been found that the values for Ps in tilted smectic liquid crystal phases in the presence of the same host substances are 50 to 100% higher compared to doping by means of the compounds mentioned, if the doping substances used are 1,3-dioxolane-4-carboxylic esters of the general formula (V)

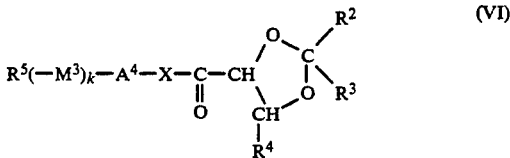

or (VI)

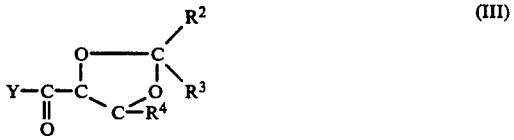

in which R¹, R², R³, R⁵, A¹, A², A³, A⁴, M¹, M², M³, X, j, k, l, m and n have the same meaning as in formula (I) and (IV) and in which R⁴ is an ethyl or vinyl radical, in which in formula (V) one or both radicals R⁴, if R¹ is a dioxolane-4-carboxyl radical, is an ethyl or vinyl radical and the other can be a radical R⁴ having the meaning given in formula (I). R² and R³ in formula (V) and (VI) are both preferably CH₃ or together with the C(2) atom of the dioxolane ring form a cyclohexane ring.

The new compounds of the formula (V), in particular (VI), preferably include the compounds mentioned by name in the examples. The compounds of the formula (V) or (VI) are prepared by reacting mesogenic phenols or thiophenols of the formula (II)

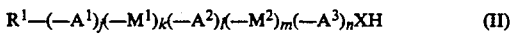 (II)

or of the formula (IIa)

R⁵(—M³)ₖ)—A⁴—XH   (IIa)

with derivatives of 5-vinyl-1,3-dioxolane-4-carboxylic acid or 5-ethyl-1,3-dioxolane-4-carboxylic acid (III)

 (III)

in which R⁴ is an ethyl or vinyl radical in the presence of condensating agents (cf. e.g. Mar., Advanced Organic Chemistry, 2nd Edition, McGraw-Hill, p. 363–365), and isolating the reaction product and purifying it, for example by recrystallization or chromatographic separation processes.

The phenols to be used as well as processes for preparing 5-vinyl-1,3-dioxolane-4-carboxylic acid and their derivatives (cf. Synthesis 1987 (9), 801–806) are known from the literature. The corresponding 5-ethyl compounds are obtained by known methods, for example by hydrogenation in the presence of a Pd/carbon catalyst.

Liquid crystal mixtures according to the invention form liquid crystal phases and contain at least one optically active compound of the general formula (V) or (VI).

The term "liquid crystal phase" is understood to mean nematic, cholesteric, orthogonally smectic or tilted smectic, in particular $S_A$, $S_B$ and $S_C$, phases. The liquid crystal mixtures consist of 2 to 20, preferably 2 to 15, components, among them at least one of the chiral compounds claimed according to the invention.

The other components are preferably selected from the known compounds which have nematic, cholesteric and/or smectic, for example $S_A$, phases, and/or tilted smectic phases; these include, for example, Schiff bases, biphenyls, terphenyls, phenylcyclohexanes, pyrimidines, cinnamic esters, cholesterol esters, various bridged polynuclear esters of p-alkylbenzoic acids which have polar end groups. In general, the commercially available liquid crystal mixtures are already present before the addition of the optically active compound(s) as mixtures of a wide range of components, of which at least one is mesogenic, that is to say, as a compound which in the form of a derivative or in a mixture with certain co-components has a liquid crystal phase which can be expected to form at least one enantiotropic (clearing temperature>melting temperature) or monotropic (clearing temperature<melting temperature) mesophase. In particular, the liquid crystal mixture contains, in addition to at least one of the optically active compounds claimed according to the invention, an ester compound having an $S_C$ phase, for example a phenyl alkoxybenzoate, or a biaromatic compound having a nitrogen-containing heterocycle, for example an alkylpyrimidinylalkoxybenzene.

Of the compound(s) according to the invention, liquid crystal mixtures in general contain 0.05 to 70% by weight, in particular 0.1 to 50% by weight. The compounds according to the invention are in particular suitable as doping substances for tilted smectic liquid crystal phases, since they convert these phases into ferroelectric liquid crystal phases; the values for spontaneous polarization (Ps) at 25° C. are in the range of about 29–38 $nC/cm^2$ for 10 mol % of doping and in the range of about 290–380 $nC/cm^2$ upon linear extrapolation to the pure compound. The switching times of the new systems are in most cases considerably below 50 μs for 10 mol % of doping, at 25° C. and a switching voltage of ±10 V/μm. The compounds according to the invention can also be used for achieving the electroclinic effect in orthogonal smectic phases ($S_A$, $S_B$, $S_E$).

EXAMPLE 1

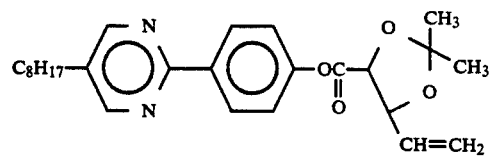

4-(5-Octylpyrimidin-2-yl)phenyl-2,2-dimethyl-5-vinyl-1,3-dioxolane-4-carboxylate. 1.72 g (10 mmol) of 2,2-dimethyl-5-vinyl-1,3-dioxolane-4-carboxylic acid are added to a solution of 2.84 g (10 mmol) of 4-(5-n-octylpyrimidin-2-yl)phenol, 10 mg of dimethylaminopyridine and 2.10 g (10 mmol) of dicyclohexylcarbodiimide in 100 ml of dichloromethane. After stirring at room temperature for 2 days, the precipitate (dicyclohexylurea) is filtered off, the filtrate is subjected to rotary evaporation and chromatographed over silica gel (hexane/ethyl acetate 85:15). Recrystallization from hexane gives 1.21 g (27% of theory) of colorless crystals.

Melting point: 62° C.
$[\alpha]_{365}^{22} = -207.8°$ (c=2, $CH_2Cl_2$)

The following are obtained analogously:

EXAMPLE 2

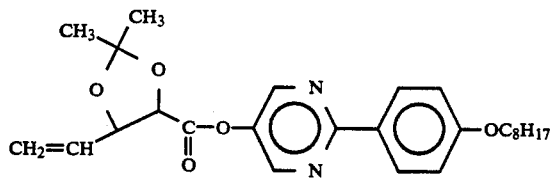

(4R,5R)-2-(4-Octyloxyphenyl)pyrimidin-5-yl 2,2-dimethyl-5-vinyl-1,3-dioxolane-4-carboxylate.

Melting point: 126° C.
$[\alpha]_{365}^{22} = -222.0°$ (c=2, $CH_2Cl_2$)

EXAMPLE 3

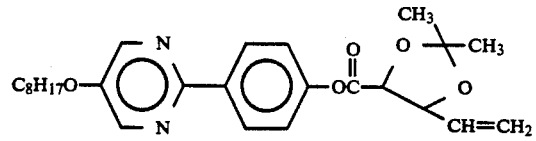

(4R,5R)-4-(5-Octyloxypyrimidin-2-yl)phenyl 2,2-dimethyl-5-vinyl-1,3-dioxolane-4-carboxylate Melting point: 94° C.
$[\alpha]_{365}^{22} = -223.8°$ (c=2, $CH_2Cl_2$)

EXAMPLE 4

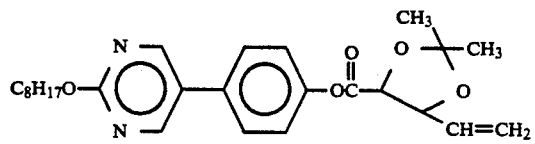

(4R,5R)-4-(2-Octyloxypyrimidin-5-yl)phenyl 2,2-dimethyl-5-vinyl-1,3-dioxolane-4-carboxylate Melting point: 121° C.
$[\alpha]_{365}^{22} = -198.1°$ (c=2, $CH_2Cl_2$)

EXAMPLE 5

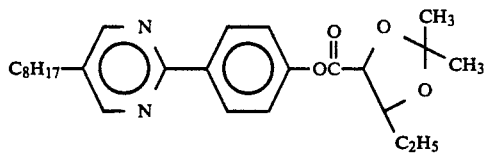

(4R,5R)-4-(5-Octylpyrimidin-2-yl)phenyl 2,2-dimethyl-5-ethyl-1,3-dioxolane-4-carboxylate
Melting point: 53° C.
$[\alpha]_{365}^{22} = -68.8°$ (c=2, $CH_2Cl_2$)

EXAMPLE 6

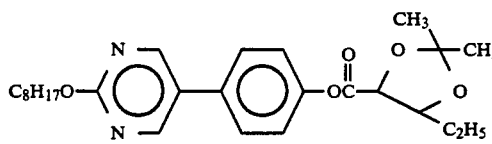

(4R,5R)-4-(5-Octyloxypyrimidin-2-yl) phenyl 2,2-dimethyl-5-ethyl-1,3-dioxolane-4-carboxylate
Melting point: 87° C.
$[\alpha]_{365}^{22} = -70.5°$ (c=2, $CH_2Cl_2$)

EXAMPLE 7

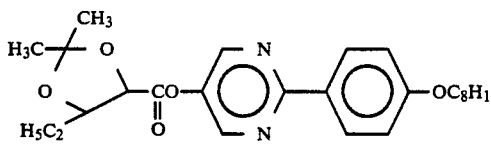

(4R,5R)-2-(4-Octyloxyphenyl)pyrimidin-5-yl 2,2-dimethyl-5-ethyl-1,3-dioxolane-4-carboxylate
Melting point: 128° C.
$[\alpha]_{365}^{22} = -63.4°$ (c=2, $CH_2Cl_2$)

EXAMPLE 8

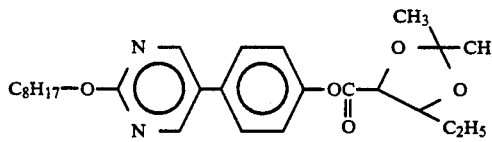

(4R,5R)-4-(2-Octyloxypyrimidin-5-yl)phenyl 2,2-dimethyl-5-ethyl-1,3-dioxolane-4-carboxylate
Melting point: 110° C.
$[\alpha]_{365}^{22} = -64.3°$ (c=2, $CH_2Cl_2$)

EXAMPLE 9

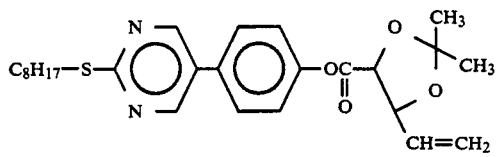

(4R,5R)-4-(2-Octylthiopyrimidin-5-yl)phenyl 2,2-dimethyl-5-vinyl-1,3-dioxolane-4-carboxylate
Melting point: 105° C.
$[\alpha]_{365}^{22} = -205.0°$ (c=2, $CH_2Cl_2$)

EXAMPLE 10

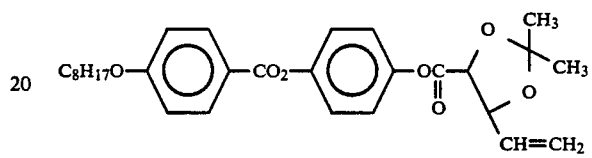

(4R,5R)-4-(4-Octyloxybenzoyloxy)phenyl 2,2-dimethyl-5-vinyl-1,3-dioxolane-4-carboxylate
Melting point: 88° C.
$[\alpha]_{365}^{22} = -148.6°$ (c=2, $CH_2Cl_2$)

EXAMPLE 11

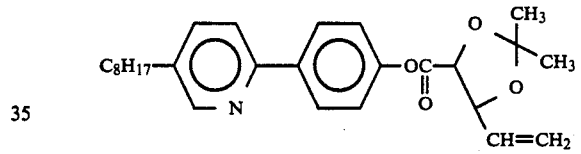

(4R,5R)-4-(5-Octylpyridin-2-yl)phenyl 2,2-dimethyl-5-vinyl-1,3-dioxolane-4-carboxylate
Melting point: 76° C.
$[\alpha]_{365}^{22} = -216.9°$ (c=2, $CH_2Cl_2$)

EXAMPLE 12

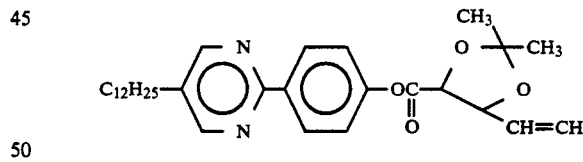

(4R,5R)-4-(5-dodecylpyrimidin-2-yl)phenyl 2,2-dimethyl-5-vinyl-1,3-dioxolane-4-carboxylate
Melting point: 59° C.
$[\alpha]_{365}^{22} = -197.8°$ (c=2, $CH_2Cl_2$)

EXAMPLE 13

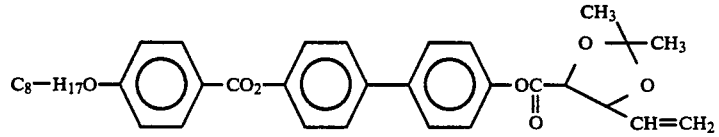

(4R,5R)-4'-(4-octyloxybenzoyloxy)biphenyl-4-yl 2,2-dimethyl-5-vinyl-1,3-dioxolane-4-carboxylate
Phase transition K 119 N 135 I
$[\alpha]_{365}^{22} = -162.2°$ (c=2, $CH_2Cl_2$)

EXAMPLE 14

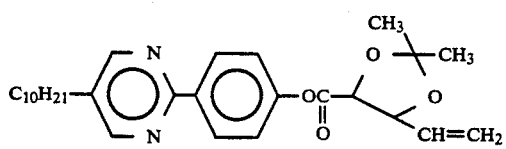

(4R,5R)-4-(5-decylpyrimidin-2-yl)phenyl 2,2-dimethyl-5-vinyl-1,3-dioxolane-4-carboxylate Melting point: 74° C.

$[\alpha]_{365}^{22} = -182.4°$ (c=2, $CH_2Cl_2$)

Method of measurement:

If a small amount of a chiral compound is added to a (non-chiral) solvent, the plane of the linearly polarized light is rotated by a (characteristic) angle α; this angle is recorded as follows:

$[\alpha]_\lambda^T$ (c=x, IS), the symbols having the following meaning: λ: wavelength [nm] of the polarized light, x=concentration of the solution in g/l, S=solvent, T=temperature of the solution. The angle of rotation is determined in a polarimeter after a light path of 10 cm.

WORKING EXAMPLES A1 to A5

To test the effect of the compounds described above as ferroelectric doping substances in liquid crystal systems which have tilted smectic phases, they are mixed in concentrations of 10 mol % each with a non-chiral test mixture having the phase sequence C 12.5° C. $S_c$ 83° C. $S_A$ 95° N 100° C. I, and the values for spontaneous polarization ($P_s$ in $nC/cm^2$) of the mixture are determined. The $P_s$ values are determined by the method of H. Diamant et al. (Rev. Sci. Instr., 28, 30, 1957), in which a special measuring cell [Skarp et al. in Ferroelectric Letters Vol. 06, 67 (1986)] is used. At a cell path length of about 2 μm, uniform planar orientation of the liquid crystals in the $S_c$ phase is achieved by shear [SSFLC Technology, Clark et al., Appl. Phys. Lett. 36, 899 (1980)]. In Table 1, the $S_c$ range of the particular mixture is listed in addition to the values for $P_s$. In the second column of Table 2, compounds according to German Patent Application P 3,713,273.3 are contrasted with compounds according to the invention (third and fourth column), in which the $P_s$ values in the same host substance at the same doping level (10 mol %) and the same temperature (25° C.) are compared. These examples show that under otherwise identical conditions the value of spontaneous polarization for the 5-ethyl and 5-vinyl compounds is 50–100% higher compared with that of the compound which is unsubstituted in the 5-position of the dioxolane ring.

TABLE 1

| Substance from Example | Working Example | C | $S_c°$ | $S_A°$ | N | I | P [$nC/cm^2$] |
|---|---|---|---|---|---|---|---|
| 5 | A1 | . | 9.5 . | 68 . | 83.5 . | 95.5 | . 36 |
| 6 | A2 | . | 12 . | 71 . | 89.5 . | 97 | . 29 |
| 7 | A3 | . | 11 . | 71 . | 88 . | 93.5 | . 33 |
| 8 | A4 | . | 11.5 . | 77 | | . 93.5 | . 31 |
| 11 | A5 | . | 12 . | 70 . | 78 . | 94 | . 35 |

An additional characteristic feature of Working Example A1 is that at such a large pitch of 7.8 μm in the nematic phase at 83.6° C. further compensation by means of a second doping substance is not necessary.

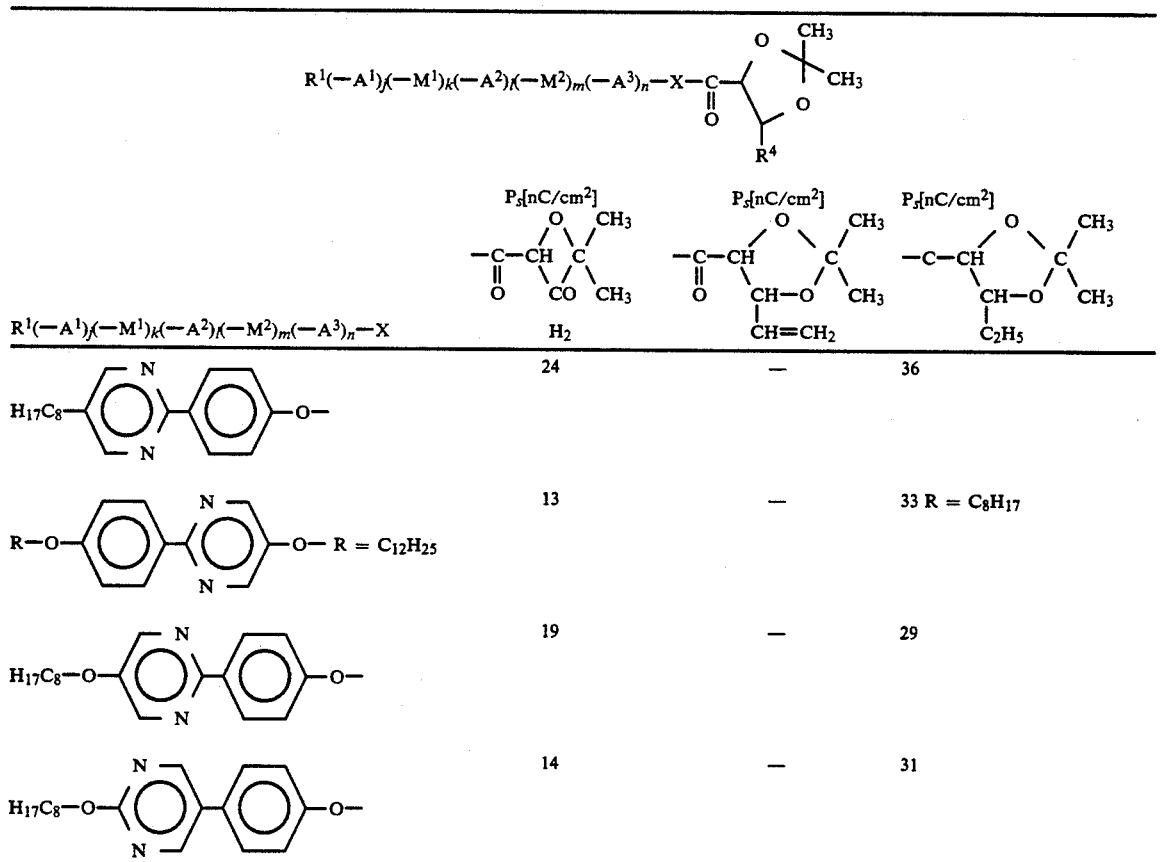

| $R^1(-A^1)_l(-M^1)_k(-A^2)_l(-M^2)_m(-A^3)_n-X$ | $P_s[nC/cm^2]$ 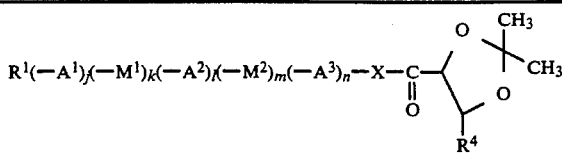 $H_2$ | $P_s[nC/cm^2]$ 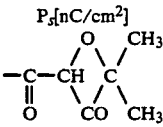 $CH=CH_2$ | $P_s[nC/cm^2]$ 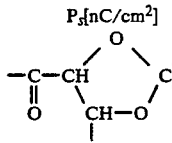 $C_2H_5$ |
|---|---|---|---|
| 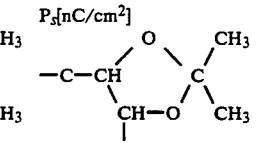 | 8 | 16 | — |
| 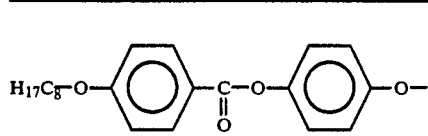 | 20,2 | 35 | — |

WORKING EXAMPLE A6

A ferroelectric mixture consisting of

| | |
|---|---|
| 5-Octyl-2-(4-hexyloxyphenyl)-pyrimidine | 14.2 mol % |
| 5-Octyl-2-(4-octyloxyphenyl)-pyrimidine | 12.5 mol % |
| 5-Octyl-2-(4-decyloxyphenyl)-pyrimidine | 9.4 mol % |
| 5-Octyloxy-2-(4-butyloxyphenyl)-pyrimidine | 9.4 mol % |
| 5-Octyloxy-2-(4-hexyloxyphenyl)-pyrimidine | 8.9 mol % |
| 5-Octyloxy-2-(4-octyloxyphenyl)-pyrimidine | 4.1 mol % |
| 5-Octyloxy-2-(4-decyloxyphenyl)-pyrimidine | 7.5 mol % |
| 4-(5-Dodecylpyrimidin-2-yl)phenyl trans-4-pentylcyclohexanecarboxylate | 14 mol % |
| (2R,3R)-4-(2-Octyloxypyrimidin-5-yl)-phenyl 3-propyloxirane-2-carboxylate | 5.4 mol % |
| (2S,3S)-2-[4-(5-Octylpyimidin-2-yl)-phenyloxy]methyl-3-butyloxirane | 13.1 mol % |
| (4R,5R)-4-(5-n-Octylpyrimidin-2-yl)-phenyl 2,2-dimethyl-5-ethyl-1,3-dioxolane-4-carboxylate | 1.5 mol % |

(doping substance according to the invention) having the following phases:
C—4 $S_c^*$ 64 $S_A^*$ 69 $N^*$ 80 I
At 20° C., this mixture has polarization of 49 nC·cm$^{-2}$.

WORKING EXAMPLE A7 a) A ferroelectric mixture consisting of the 7 components

| | |
|---|---|
| 5-Octyloxy-2-(4-hexyloxyphenyl)-pyrimidine | 23 mol % |
| 5-Octyloxy-2-(4-octyloxyphenyl)-pyrimidine | 10.6 mol % |
| 5-Octyloxy-2-(4-butyloxyphenyl)-pyrimidine | 24.3 mol % |
| 5-Octyloxy-2-(4-decyloxyphenyl)-pyrimidine | 19.3 mol % |
| 4-(5-Decylpyrimidin-2-yl)phenyl trans-4-pentylcyclohexanecarboxylate | 13.8 mol % |
| (2R,3R)-4-(2-Octyloxypyrimidin-5-yl)-phenyl 3-propyloxirane-2-carboxylate | 2 mol % |
| Compound from Example 5 | 7 mol % | has the following phase sequence:
C 9 $S_c$ 71 $S_A$ 85 N 96 I

The spontaneous polarization at 20° C. is 43 nC·cm$^{-2}$ and the switching time at a field of 10 V·μm$^{-1}$ is ($\gamma$0.90) 74 μs.

WORKING EXAMPLE A8 a) A ferroelectric mixture consisting of the 8 components

| | |
|---|---|
| 5-Octyloxy-2-(4-hexyloxyphenyl)-pyrimidine | 24.8 mol % |
| 5-Octyloxy-2-(4-octyloxyphenyl)-pyrimidine | 11.5 mol % |
| 5-Octyloxy-2-(4-butyloxyphenyl)-pyrimidine | 26.2 mol % |
| 5-Octyloxy-2-(4-decyloxyphenyl)-pyrimidine | 20.8 mol % |
| 4-(5-Decylpyrimidin-2-yl)phenyl trans-4-pentylcyclohexanecarboxylate | 14.7 mol % |
| (2S,3S)-(—)-2-[4-(5-Octylpyrimidine-2-yl)phenyloxy]methyl-3-butyloxirane | 1.5 mol % |
| (2R,3R)-4-(2-Octyloxypyrimidin-5-yl)-phenyl 3-pentyloxirane-2-carboxylate | 0.46 mol % |
| Compound of Example 5 | 0.04 mol % | has the following liquid-crystalline phase regions:
C 9 $S_c^*$ 80.4 $S_A^*$ 90 $N^*$ 102.5 I
and has a spontaneous polarization of 5.6 nC·cm$^{-2}$ at 25° C. and a switching time of ($\gamma$0.90) of 190 μs. At a temperature of 95° C., the pitch of this mixture >50 μm.

The switching time $\gamma_{0.90}$ is determined by means of a photodiode by measuring the build-up time of the light signal from a signal height of 10 to 90%. The switching voltage consists of square-wave pulses and is ±10 V·μm$^{-1}$.

WORKING EXAMPLE A9

A ferroelectric mixture consisting of

| | |
|---|---|
| 5-Octyl-2-(4-hexyloxyphenyl)-pyrimidine | 13.1 mol % |
| 5-Octyl-2-(4-octyloxyphenyl)-pyrimidine | 11.6 mol % |
| 5-Octyl-2-(4-decyloxyphenyl)-pyrimidine | 8.7 mol % |
| 5-Octyloxy-2-(4-butyloxyphenyl)-pyrimidine | 8.7 mol % |
| 5-Octyloxy-2-(4-hexyloxyphenyl)-pyrimidine | 8.2 mol % |
| 5-Octyloxy-2-(4-octyloxyphenyl)-pyrimidine | 3.8 mol % |
| 5-Octyloxy-2-(4-decyloxyphenyl)-pyrimidine | 7 mol % |
| 4-(5-Dodecylpyrimidin-2-yl)phenyl trans-4-pentylcyclohexanecarboxylate | 13 mol % |
| 4-(5-Decylpyrimidin-2-yl)phenyl trans-4-pentylcyclohexanecarboxylate | 3.9 mol % |
| (S)-4-(2-Octyloxypyrimidin-5-yl)phenyl [spiro-(1,3-dioxolane-2,1'-cyclohexane)-4-yl]methyl ether | 10 mol % |
| (2S,3S)-2-[4-(5-Octylpyrimidin-2-yl)-phenyloxy]methyl-3-butyloxirane | 10 mol % |
| (4R,5R)-4-(5-n-Octylpyrimidin-2-yl)-phenyl 2,2-dimethyl-5-ethyl-1,3-dioxolane-4-carboxylate (doping substance according to the invention) | 2 mol % | has the following phases:
C $-2$ $S_c^*$ 60 $S_A^*$ 70 $N^*$ 78 I

At 25° C., this mixture has a polarization of 50 nC·cm$^{-2}$·cm and a switching time ($\gamma_{0.90}$) of 44 μs at a field of 10 V·μm$^{-1}$.

We claim:

1. A method for increasing spontaneous polarization of a liquid crystal mixture, which comprises adding an optically active 1,3-dioxolane-4-carboxylic ester of the formula (V) to the mixture $$R^1(-A^1)_j(-M^1)_k(-A^2)_l(-M^2)_m(-A^3)_n-X- \quad (V)$$

$$-\overset{O}{\underset{\|}{C}}-CH^*\begin{array}{c}O\\ \diagdown \\ \diagup \\ O\end{array}\overset{R^2}{\underset{R^4}{\overset{|}{C}-R^3}}$$

in which the symbols have the following meaning:
$R^1$ is $$-O-\overset{O}{\underset{\|}{C}}-CH\begin{array}{c}O\\ \diagdown \\ \diagup \\ O\end{array}\overset{R^{2'}}{\underset{R^{4'}}{\overset{|}{C}-R^{3'}}} \quad \text{or} \quad (Va)$$

a straight-chain or branched alkyl radical having 1 to 16 carbon atoms or a straight-chain or branched alkenyl radical having 2 to 16 carbon atoms, it being possible for these radicals themselves to contain asymmetric carbon atoms, in which one or more non-adjacent —CH$_2$— groups can be replaced by $$-O-, -S-, -\overset{O}{\underset{\|}{C}}-, -O-\overset{O}{\underset{\|}{C}}- \text{ and/or } -\overset{O}{\underset{\|}{C}}-O-$$

one or more H can be replaced by F, Cl, Br or CN,
$R^2$, $R^{2'}$, $R^3$ and $R^{3'}$ are each H or an alkyl radical having 1 to 10 carbon atoms, in which one or more H can be replaced by F, or $R^2$ and $R^3$ or $R^{2'}$ and $R^{3'}$ together with the C(2) atom of the dioxolane ring form a cyclopentane, cyclohexane or cycloheptane ring, $R^4$, $R^{4'}$ are vinyl or ethyl, or, if $R^1$ is a radical of the formula (Va), H or an alkyl radical having 1 to 10 or an alkenyl radical having 2 to 10 carbon atoms, with the proviso that at least one radical $R^4$, $R^{4'}$ is vinyl or ethyl, j and l are zero, 1 or 2, k and m are zero or 1, n is zero, 1 or 2, with the following proviso: if j and/or l are zero, k is zero; if n is zero, m is zero; the sum j+l+n is at least 2 and at most 3, —A$^1$ and —A$^2$ are

[chemical structures: phenyl, cyclohexyl, pyridyl, pyrimidinyl, pyridazinyl, pyrazinyl, triazinyl variants; dioxane/dithiane/oxathiane rings; thiophene and related S,N heterocycles]

$$-N\begin{array}{c}\diagup\\ \diagdown\end{array}N-$$

—A$^3$ is

[chemical structures: phenyl, cyclohexyl, pyridyl, pyrimidinyl, pyridazinyl variants]

—M$^1$ and —M$^2$ are

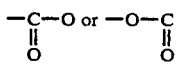

and X is O.

2. The method for increasing spontaneous polarization of a liquid crystal mixture, which comprises adding an optically active 1,3-dioxolane-4-carboxylic ester of the formula (VI) to the mixture

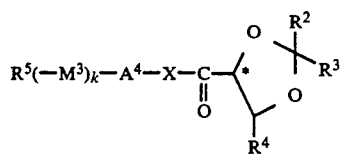 (VI)

in which the symbols have the following meaning:

$R^2$ and $R^3$ have the same definition as in claim 1, X is O, $R^4$ is vinyl or ethyl, $R^5$ is a straight-chain or branched alkyl or alkenyl radical having 6 to 12 carbon atoms, which can contain an asymmetric carbon atom, —$M^3$ is

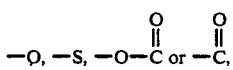

—$A^4$ is

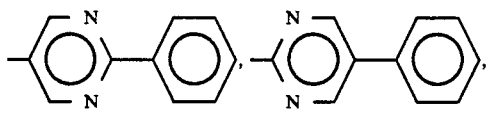

-continued

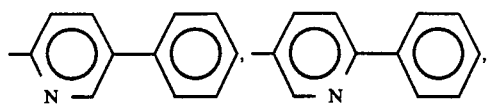

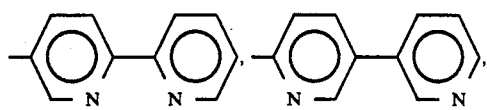

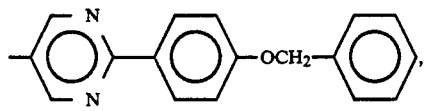

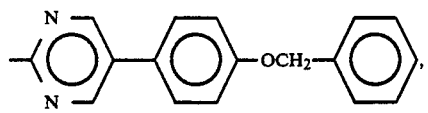

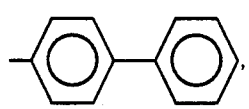

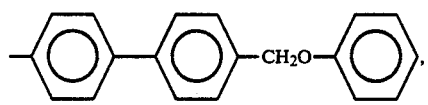

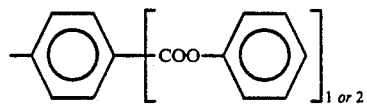

3. A method as claimed in claim 2, wherein $R^2$ and $R^3$ are each —$CH_3$.

* * * * *